US00PP11594P

United States Patent [19]

Olesen et al.

[11] Patent Number: Plant 11,594

[45] Date of Patent: Oct. 24, 2000

[54] MINIATURE ROSE PLANT NAMED 'POULFIO'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/113,421

[22] Filed: Jul. 10, 1998

[51] Int. Cl.[7] ..... A01H 5/00

[52] U.S. Cl. ..... Plt./121

[58] Field of Search ..... Plt./116, 120, 121, Plt./122

[56] References Cited

U.S. PATENT DOCUMENTS

P.P. 10,934 6/1999 Olesen et al. ..... Plt./121

*Primary Examiner*—Howard J. Locker

[57] ABSTRACT

A new miniature pot rose plant which has abundant, durable, salmon pink-colored flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present discovery constitutes a new and distinct variety of a miniature pot rose plant which was discovered in a cultivated area. The mutation resulted from 'POULlak', a miniature pot rose hybridized by the same inventors. 'POULlak' is described and illustrated in U.S. Plant Pat. No. 10,934. The new rose variety resulted from a naturally occurring mutation of unknown causation on a branch of 'POULlak' which was discovered in a controlled planting.

The rose plant of the present discovery has a unique combination of characteristics which are outstanding in the new variety and which distinguish it from the original rose 'POULlak' as well as all other varieties which we are aware of. For example, the new variety has:

1. Abundant salmon pink-colored flowers;
2. Vigorous and compact growth;
3. Year-round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and distinguish 'POULfio' from all other varieties of which we are aware.

Asexual reproduction of 'POULfio' by cuttings was first done by L. Pernille and Mogens N. Olesen in their nursery in Fredensborg, Denmark in March, 1996. This initial and other subsequent propagations conducted in controlled environments have demonstrated that the characteristics of 'POULfio' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULfio'. Specifically illustrated in SHEET 1:

1. Stem or entire plant showing branching and the attachment of leaves, buds and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULfio', as observed in its growth in glasshouses in Fredensborg, Denmark and Half Moon Bay, Calif. and in field nursery in Jackson County, Ore. Color references are made using The Royal Horticultural Society (London, England) Colour Chart, 1995, except where common terms of color are used.

For a comparison, the nearest existing rose variety is 'POULlak', a miniature rose variety described and illustrated in U.S. Plant Pat. No. 10,934, granted Jun. 1, 1999. Chart 1 details several physical characteristics of POULfio and POULlak.

CHART 1

| | 'POULfio' | 'POULlak' |
|---|---|---|
| Bud color at ¼ open | Red Group 52B | Red Group 39D |
| Color of upper surface of flower petal on an open flower | Red Group 52C | Red Group 49B |
| Color of reverse surface of flower petal on an open flower | Red Group 52C | Red Group 38C |

Parentage: Mutation of 'POULlak'.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 12 mm–16 mm in length.
*Bud form.*—Pointed to pointed ovoid.
*Bud color.*—Red Group 52B at ¼ opening.

*Sepals.*—Green Group 137A to 137B. Weak foliaceous appendages on three of the five sepals. Surfaces of sepals moderately pubescent. Limited numbers of stipitate glands present on sepals with appendages.

*Peduncle.*—Surface: Smooth. Length: 25–45 mm average length. Color: Green Group 137C. Strength: Erect.

*Receptacle.*—Surface: Smooth. Shape: Funnel-shaped. Size: Small. 4 mm×4 mm. Color: Green Group 137C.

*Borne.*—Generally 1–3 buds per flowering stem.

Flower bloom:

*Size.*—Small for a 10 cm pot rose. Average diameter is 35 mm when open.

*Form.*—Upon opening, form of upper part of flower is flat. Completely open, form of upper part of flower is a flattened convex. Completely open, form of lower half of flower is flat.

*Petalage.*—Double. Average range: 40–45 under normal conditions.

*Color.*—Upon opening, the upper surface of the petals is Red Group 52B. Upon opening, the reverse side is Red Group 52B. After opening, the upper surface of the petal is Red Group 52C. After opening, the reverse surface of the petal is Red Group 52C. Upon opening, a petal spot Green-Yellow Group 1C exists on the inner and outer bases of the petals. After opening, the petal spot is Green-Yellow Group 1D on the inner and outer bases of the petals.

*Discoloration.*—No change in the general tonality after three days. Thereafter, general tonality changes slightly to Red Group 41D.

*Petal reflex.*—Most petals reflex backwards slightly.

*Petaloids.*—Present. 4–6 per bloom.

*Fragrance.*—Light.

*Duration.*—As a pot plant, flowers last from 16 to 18 days. As a cut flower, 8 to 10 days.

Petals:

*Texture.*—Thin.

*Shape.*—Oval. Many of the petal margins terminate with a point in the center.

*Form.*—Reflexed slightly.

*Arrangement.*—Normal.

Reproductive organs:

*Pollen.*—Color: Yellow-Orange Group 20A. Abundance: Limited.

*Anthers.*—Size: Medium. Color: Green-White Group 157A. Abundance: Limited.

*Filaments.*—Color: Yellow-Green Group 150D.

*Stigmas.*—Position is slightly superior to anthers. Color: Green-White Group 157B.

*Styles.*—Color: Green-White Group 157B.

PLANT

Plant growth: Vigorous and compact. Upright to bushy. When grown as a 10 cm pot plant, the average height of the plant itself is 18–20 cm and the average width is 18–20 cm. When grown as a nursery plant on its own roots the average plant height is 25–30 cm and the average plant width is 18–22 cm.

Stems:

*Color.*—Young wood: Green Group 138B. Older wood: Green Group 138B.

*Thorns.*—Incidence: Average number of thorns. Size: Average length: 2 mm–4 mm. Color: Most thorns Orange-White Group 159A, some with intonation of Red Group 37D. Shape: Linear.

*Bark.*—Young wood: Smooth. Older wood: Smooth.

Plant foliage: Normal number of leaflets on normal leaves in middle of the stem: 5 leaflets.

*Leaf size.*—Small. 60 mm×35 mm.

*Abundance.*—Above average.

*Color.*—Upper Leaf Surface: Yellow-Green Group 147A. Lower Leaf Surface: Green Group 138B. Juvenile foliage: Green Group 143C to Yellow-Green Group 144A. Anthocyanin intonation: Present on the lower surfaces of leaflets, the upper sides of the rachis, the leaflet margins, and the margins of sepals.

Plant leaves and leaflets;

*Stipules.*—Present. Hairs present on margins. Size: To 8 mm in length. Color: Yellow-Green Group 147A.

*Petiole.*—Margins with stipitate glands. Length: 12–15 mm. Underneath: With hairs and prickles. Color: Yellow-Green Group 147A.

*Rachis.*—With prickles underneath. Margins with stipitate glands. Color: Yellow-Green Group 147A. Upper surface with intonation of Greyed-Red Group 178C.

*Leaflet edge.*—Finely serrated.

*Shape.*—Leaflets are ovate.

*Leaflets.*—Number: Generally 5.

*Other.*—Matte finish. Thin texture.

Disease resistance: Above-average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant salmon pink-colored flowers, compact and vigorous growth, year round flowering under glasshouse conditions, suitability for production from softwood cuttings in pots, and durable flowers and foliage which make the variety suitable for distribution in the floral industry.

* * * * *

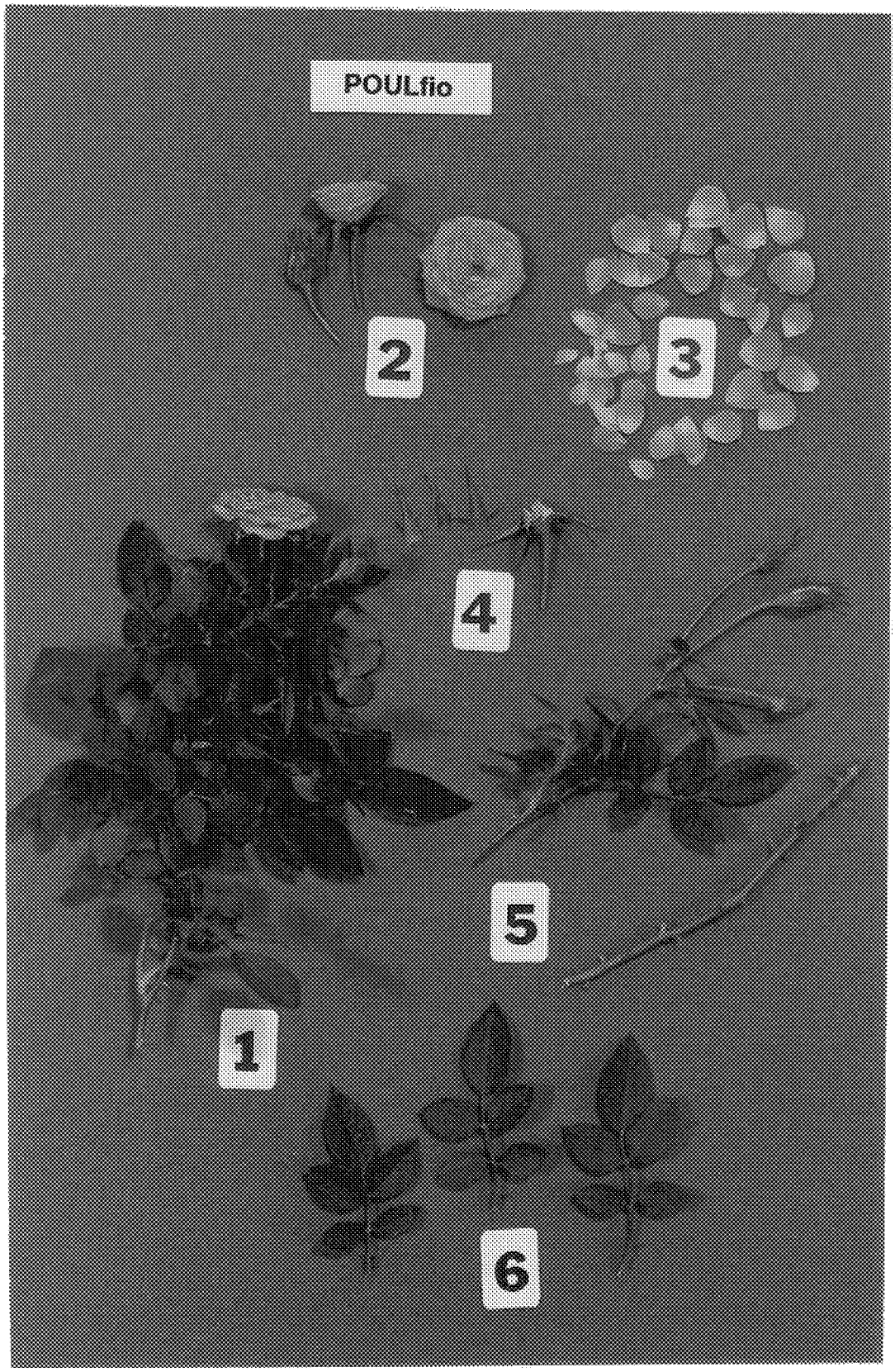
POULfio
2
3
4
5
1
6